US012533307B2

(12) United States Patent
Nevermann et al.

(10) Patent No.: US 12,533,307 B2
(45) Date of Patent: Jan. 27, 2026

(54) COMPOSITIONS FOR CLEANING SKIN AND/OR HANDS COMPRISING LEMON JUICE OR LEMON JUICE CONCENTRATE

(71) Applicant: MENNO CHEMIE-VERTRIEB GMBH, Norderstedt (DE)

(72) Inventors: Jan Nevermann, Hamburg (DE); Wolfgang Zerling, Kaltenkirchen (DE)

(73) Assignee: MENNO CHEMIE-VERTRIEB GMBH, Norderstedt (DE)

( * ) Notice: Subject to any disclaimer, the term of this patent is extended or adjusted under 35 U.S.C. 154(b) by 428 days.

(21) Appl. No.: 18/018,945

(22) PCT Filed: Jun. 16, 2021

(86) PCT No.: PCT/EP2021/066235

§ 371 (c)(1),
(2) Date: Jan. 31, 2023

(87) PCT Pub. No.: WO2022/037821

PCT Pub. Date: Feb. 24, 2022

(65) Prior Publication Data

US 2023/0293413 A1 Sep. 21, 2023

(30) Foreign Application Priority Data

Aug. 20, 2020 (EP) .................................... 20192008

(51) Int. Cl.

| | |
|---|---|
| ***C11D 1/37*** | (2006.01) |
| ***A61K 8/02*** | (2006.01) |
| ***A61K 8/34*** | (2006.01) |
| ***A61K 8/39*** | (2006.01) |
| ***A61K 8/46*** | (2006.01) |
| ***A61K 8/96*** | (2006.01) |
| ***A61Q 19/10*** | (2006.01) |

(52) U.S. Cl.

CPC ............ *A61K 8/466* (2013.01); *A61K 8/0208* (2013.01); *A61K 8/347* (2013.01); *A61K 8/39* (2013.01); *A61K 8/463* (2013.01); *A61K 8/96* (2013.01); *A61Q 19/10* (2013.01); *A61K 2800/48* (2013.01); *A61K 2800/596* (2013.01)

(58) Field of Classification Search

CPC .... C11D 1/12; C11D 1/29; C11D 1/37; C11D 1/72; C11D 1/83; C11D 3/0094; C11D 3/3418; C11D 3/382; C11D 7/44

See application file for complete search history.

(56) References Cited

U.S. PATENT DOCUMENTS 6,153,208 A * 11/2000 McAtee .................. A61K 8/44 424/59
2004/0028712 A1* 2/2004 Shepherd, Jr. ....... A61K 36/736 424/114
2005/0129643 A1* 6/2005 Lepilleur ............... A61K 8/898 424/70.1
2012/0245205 A1* 9/2012 Delong ................ A61K 31/585 514/342
2012/0321577 A1* 12/2012 Lee .......................... A61K 8/44 424/62
2014/0242198 A1* 8/2014 Modak .................. A01N 31/08 424/770
2015/0098745 A1* 4/2015 Brown ..................... C11D 3/32 401/196
2017/0009187 A1* 1/2017 Gorra ................... C11D 3/2079
2022/0117869 A1* 4/2022 Crudden ................ A61K 8/368

FOREIGN PATENT DOCUMENTS

CN 104116659 A 10/2014
CN 1104116664 A 10/2014
CN 111286425 A 6/2020
DE 19927936 A1 12/2000
DE 102005056289 A1 5/2007
GB 2010892 A 7/1979

OTHER PUBLICATIONS

Database GNPD [Online] Mintel; Aug. 8, 2018 (Aug. 8, 2018, anonymous: "Germ Protection Hand Wash", XP93099385, Database accession No. 5885873.

Cassiday Laura: "Surfactants and Skin", International News on Fats, Oils, and Related Materials (INFORM), Jan. 1, 2016 (Jan. 1, 2016), Seiten 694-600, XP93099604, U.S.A. Gefunden im Internet: URL: https://www.aocs.org/ documents/InformPDF/Inform_JAN_2016.pdf (gefunden am Nov. 9, 2024}.

Effendy and Maibach: Surfactants and experimental irritant contact dermatitis:, Contact Dermatitis, Bd. 33, Jan. 1, 1995 (Jan. 1, 1995), Seiten 217-225, XP055127310, DOI: 10.1111/j.1600-0536.1995.tb00470x.

Anonymous. "Antibacterial Handwash with Lime & Lemon" Apr. 7, 2014 (Apr. 7, 2014), abstract No. Database accession No. 2338270, Retrieved from: GNPD [online] Mintel XP055833637.

* cited by examiner

*Primary Examiner* — Charles I Boyer

(74) *Attorney, Agent, or Firm* — Dickinson Wright PLLC

(57) ABSTRACT

The present invention relates to a lemon juice-containing composition and its use for cleaning skin and/or hands. The composition comprises 5-30% by weight lemon juice or a lemon juice concentrate, 0.5-10% by weight phenoxyethanol, 2-60% by weight anionic surfactant and ad 100% by weight water. The composition is particularly suitable for the effective but at the same time skin-friendly removal of contaminants containing chlorophyll and/or other plant dyes, of plant juices/extracts and/or other plant parts, such as flower pollen and/or plant dusts, and/or of phytopathogens, fertilizer residues, herbicides, bactericides, fungicides, virucides and germination inhibitors.

15 Claims, No Drawings

COMPOSITIONS FOR CLEANING SKIN AND/OR HANDS COMPRISING LEMON JUICE OR LEMON JUICE CONCENTRATE

CROSS-REFERENCE TO RELATED APPLICATIONS

This application is a U.S. National Stage of International Application No. PCT/EP2021/066235, filed on Jun. 16, 2021, which claims the benefit and priority of European Patent Application No. 20192008.9, filed on Aug. 20, 2020, the entire contents of which are incorporated herein by reference.

The present invention relates to ecologically favourable agents for cleaning skin and/or hands, which are improved in their cleaning effect. The field of application of the present invention therefore lies in particular in the field of hygienic removal of organic and/or inorganic soiling from the skin, which occurs in particular in persons working in agriculture, horticulture, vegetable production, food processing of plant products, or in meristem or plant breeding company.

The composition according to the invention is based on a synergistically effective mixture of lemon juice or lemon juice concentrate (from the Rutaceae family), phenoxyethanol and surfactants. The composition according to the invention is very effective in its efficacy, but is also characterised by ecologically and dermatologically favourable properties due to the use of an exclusively water-based composition.

STATE OF THE ART

People who work in agriculture, horticulture, vegetable production, food processing of plant products or in meristem or plant breeding companies have special requirements for cleaning agents for skin and hands. Due to the frequent contact with coloured soiling, the hands are particularly stressed. The chlorophyll-containing dirt not only contains plant dyes, but also residues of pesticides and other auxiliary substances (fertilisers, herbicides, bactericides, germination inhibitors, fungicides, etc.) that affect the stratum corneum of the skin in an indefinable way.

The stratum corneum consists of two components, the corneocytes (protein-rich horny cells) and a lipophilic intercellular substance. Together with fat and water, these form the epidermis, the protective layer of the skin. With constant contact with the environment, the skin of the hands in particular is subject to great stress.

A particularly visible example of the intensive interaction between the plant and the skin is revealed by the pinching out tomato plants. Pinching out is the breaking off of certain shoots that deprive the growing fruit of parts of the nutrient salts and water. Such a shoot is referred to in technical terminology as a stingy shoot and its removal is therefore called pinching out.

Chlorophyll-containing dyes penetrate deep into the upper layers of the skin and can only be removed with the help of aggressive aids, whereby the continuous work-related repetitions cause severe stress to the epidermis. This can lead to pathological changes of the skin surface.

Thus, a cleaning agent for the skin or hands that is effective but also well tolerated is needed, especially when used frequently.

Therefore, it has been searched for a dermatologically and ecologically favourable formulation that is skin-friendly and meets the requirements of those concerned, but on the other hand is also effective in its cleaning action and also strong enough to thoroughly remove the accumulated residues from the use of the farm's by-products and auxiliary products.

A solution to these problems has not been in sight so far. Various surfactant preparations could not achieve a sufficient effect.

Another problem with prior art cleaning formulations is that they contain alcohols and/or perfumes which interact with the plant and plant products (fruit, vegetables, etc.) to cause residues and/or odour impairments and/or in turn lead to residue-relevant considerations. Both residues and/or odour impairments can be an exclusion criterion for the suitability of the herbal product in processing or for sale.

In addition, the idea of sustainability and suitability for an ecological production chain are becoming increasingly important. The aim is to use only a minimum of synthetic chemical components in such products.

It is also of particular importance that plants, plant parts, seeds, pollen and in particular plant juice are also significantly responsible for the transmission of phytopathogenic bacterial, fungal and viral pathogens. Such contamination must be effectively removed from the skin to prevent further transmission. Such pathogens can be an additional complication for hand disinfection.

Therefore, targeted hygienic hand washing and hand cleaning is essential. Plant residues, plant parts, seeds, pollen and, in particular, plant juice represent a particularly strongly adsorptive, specific and tenacious form of contamination compared to human skin, which is particularly difficult to remove and cannot be removed sufficiently thoroughly with the surfactants, detergents and hand soaps commonly used to date. If these plant-specific soils remain on the human skin, subsequent disinfection is also only possible to a limited extent and only to a greatly reduced extent due to the plant-specific soils.

If hygienic hand washing or hand cleaning cannot be carried out sufficiently, there is a risk of residues (fertilisers, herbicides, bactericides, germicides, fungicides, etc.), but also alcoholic and chemically synthetic components (perfumes) and ultimately also microorganisms being transmitted as a result of insufficient subsequent hand disinfection.

Some products for hygienic hand cleaning are already known in the state of the art. However, these meet neither the high ecological nor the dermatological requirements.

Document DE 199 27 936 A1 discloses disinfectant compositions containing synergistically active combinations of fruit juices of lemon and/or orange and/or *Citrus grandis* in compounds with alkyl sulphonates and/or alkyl aryl sulphonates or sulphates, or fatty alcohol ether sulphates.

Furthermore, the product "Maxi-Grabbs", (23 Feb. 2019, pp. 1-3, XP055773572, Amazon website, URL: https://www.amazon.de/Handreinigungst%C3% BCcher-Maxi-Grabbs-90-St%C3%BCck-Werkstatt/dp/B07P2TLC7Z/ref=sr_1_101?dchild=1&keywords=TECHNOLIT&qid=1612802128&sr=8-101), discloses so-called "Maxi-Grabbs", hand cleaning cloths comprising a cloth having a composition containing phenoxyethanol, oil from the peel of sweet oranges, cationic and non-ionic surfactants, further preserving agents, and exclusively alcohol as solubiliser (methoxymethyl butanol). Furthermore, the disclosed cloths contain linalool, a-hexylcinnamaldehyde and d-limonene, among others. These ingredients and the use of alcohol as a solubiliser may cause allergic reactions and skin irritations.

It is therefore the object of the present invention to eliminate the known problems from the prior art and to provide ecologically and dermatologically favourable agents, but at the same time effective agents for cleaning and decontaminating the skin and/or the hands.

DESCRIPTION OF THE PRESENT INVENTION

According to the invention, this problem is solved by a composition comprising lemon juice (from the Rutaceae family) or its concentrate, phenoxyethanol, at least one anionic surfactant and water. Surprisingly, it was found in accordance with the invention that mixtures of surfactants in combination with phenoxyethanol and the addition of natural lemon juice have an outstanding cleaning effect on the skin with simultaneous skin care. The use of lemon juice, which is intended for human consumption, particularly emphasises the favourable ecological and toxicological properties.

The present invention thus provides a composition for cleaning the skin and/or hands which has been shown to be particularly advantageous for removing the contaminants in question from the skin, for example from the hands.

The composition according to the invention comprises the following components:

at least 5% by weight, preferably 5-30% by weight, lemon juice or lemon juice concentrate 0.5-10% by weight of phenoxyethanol, at least 2% by weight, preferably 2-60% by weight, of an anionic surfactant or a mixture of two or more anionic surfactants, and ad 100% by weight water.

The composition according to the invention (also referred to herein as the agent) is characterised by a beneficial effect in removing organic and/or inorganic soiling from the skin.

The composition according to the invention is therefore used in particular for removing pollution containing chlorophyll and/or other plant dyes and/or plant juices/extracts. Similarly, the composition according to the invention can be used for removing phytopathogens, fertilizer residues, herbicides, bactericides, fungicides, antivirals and/or germ inhibitors from the skin.

The compositions according to the invention are characterised by a high, but at the same time gentle cleaning and decontamination effect. Compared to conventional agents, the compositions according to the invention lead to the desired success in a significantly shorter time.

The composition according to the invention comprises lemon juice or lemon juice concentrate. The lemon juice is thus of natural origin. The lemon juice may be free from pulp, i.e. it contains less than 2% by weight, in particular less than 1% by weight pulp. The pulp may be removed, for example, by filtration, sieving or sedimentation of the raw juices.

Pulp in the sense of the present invention means long-fibre, solid components of the fruit pulp, which are obtained, for example, during the squeezing of the citrus fruits in addition to the fruit juice. Long fibrous components in the sense of the present invention are preferably those with a length of at least 0.5 mm, even more preferably at least 1 mm.

The lemon juice used according to the invention, usually contains 3 to 8% by weight, preferably 4 to 7% by weight, of citric acid and preferably have a pH in the range of 1 to 5, more preferably in the range of 2 to 4. The average pH value may be, for example, 3.

The lemon juice selected for the composition according to the invention is preferably juice obtained from fresh fruit, optionally treated with an enzyme, for example pectinase, to clarify the fruit juice. Preferably, the transmission at 650 nm of the juice thus obtained, at 8° Brix, is at least 80%, still more preferably at least 90%. The lemon juice or its concentrate may also have been preserved by means of a suitable, preferably a physical, measure. Examples are sterilisation or pasteurisation.

According to the invention, it should also not be excluded that an acid that is harmless to humans and/or an acid that is approved in the food industry is added to the lemon juice. Such acids include, but are not limited to, citric acid and malic acid.

Besides the natural citric acid, citrus fruits contain terpenes, the main component (70 to 90% of citrus oils) being R(+)limonene. Other typical aroma substances of citrus fruits include the aldehydes octanal, nonanal as well as α-pinene, valencene, α- and β-sinensal and also neral and geranial. In addition, such juices are rich in vitamin C, which has a positive effect on skin care and has antioxidant properties.

It is therefore essential that the entire lemon juice suitable for human consumption, among other things, is used according to the invention. The fruit juice may have a high water content, for example in the range of 75 to 95% by weight. Therefore, it is also provided according to the invention that the lemon juice may be concentrated.

Lemon juice concentrates according to the invention may be 1-10 times concentrates, preferably 2-8 times, still more preferably 3-7 times concentrates of the or the original lemon juice. The total acid mass of such concentrates may preferably be in the range of 75 to 770 g per litre, still more preferably in the range of 150 to 620 g per litre. For example, it may be 500 g per litre. The density of such concentrates, at 20° C., may preferably be in the range of 0.8 to 1.6, still more preferably in the range of 1 to 1.4.

A lemon juice or concentrate thereof for use in the composition according to the invention may be prepared, for example, by a method comprising the following steps: Squeezing the preferably washed citrus fruits by means of a juice separator and optionally concentrating the lemon juice thus obtained. Concentration is carried out in a manner known per se to the desired volume as specified above, so as to obtain a concentrate of the lemon juice.

After squeezing in a juice separator, the resulting juice can be fed into a cyclone filter, for example, to remove seeds in the juice, if required. Afterwards, the juice can be fed into a separator, for example, to separate the pulp, if desired.

Optional sterilisation can be carried out, for example, under the following conditions: Preheating the juice or its concentrate to a temperature in the range of 55 to 60° C. for degassing, then raising and the temperature to a range of 75 to 85° C. and holding this temperature for preferably 20 to 60 seconds for sterilisation and inactivation of enzymes. The liquid is then cooled to below 15° C.

If favoured, an acid that is harmless to humans and approved in the food industry can be added to the juice or concentrate. This acid can also be citric acid. However, the addition of one or more such acids is preferably a maximum of 1% by weight, even more preferably a maximum of 0.5% by weight or a maximum of 0.3% by weight, based on the raw juice obtained from the citrus fruits.

For standardisation, the lemon juice obtained is subjected to an acid test and its citric acid content is determined. The content of citric acid in the juice before its optional concentration should be in the range of 3 to 8% by weight, preferably in the range of 4 to 7% by weight.

The total acid mass of the concentrate obtainable therefrom should preferably be in the range of 75 to 770 g per litre, still more preferably in the range of 150 to 620 g per litre. The density of such concentrates, at 20° C., should preferably be in the range of 0.8 to 1.6, still more preferably in the range of 1 to 1.4. The pH of the concentrate should preferably be in the range of 1 to 5, more preferably in the range of 2 to 4.

Clarified concentrate or juice should, at 8° Brix, preferably have a transmission at 650 nm of at least 80%, even more preferably at least 90%.

The proportion of lemon juice or lemon juice concentrate in the composition according to the invention is at least 5% by weight, preferably from 5% to 30% by weight, more preferably from 7% to 25% by weight, and even more preferably from 10% to 20% by weight.

The lemon juice preferably contains 3 to 8% by weight, more preferably 4 to 7% by weight, of citric acid and preferably has a pH in the range of 1 to 5, more preferably in the range of 2 to 4. The lemon juice may be free of pulp. Lemon juice concentrates preferred according to the invention are 1-10 times concentrates, preferably 2-8 times, still more preferably 3-7 times concentrates.

The lemon juice or its concentrate may have been prepared as described above or may be obtainable by this method.

The total acid mass of the lemon juice concentrate is preferably in the range of 75 to 770 g per litre, still more preferably in the range of 150 to 620 g per litre. The density of such concentrates, at 20° C., may preferably be in the range of 0.8 to 1.6, still more preferably in the range of 1 to 1.4. The pH of the concentrates should preferably be in the range of 1 to 5, more preferably in the range of 2 to 4.

Clarified lemon juice concentrate or lemon juice should, at 8° Brix, preferably have a transmission at 650 nm of at least 80%, even more preferably of at least 90%.

The proportion of lemon juice or lemon juice concentrate in the composition according to the invention may be 5 to 30% by weight, preferably 7 to 25% by weight, more preferably 10 to 20% by weight.

The composition according to the invention further comprises phenoxyethanol. This is an ether of phenol with ethylene glycol of the molecular formula $C_8H_{10}O_2$. The proportion of phenoxyethanol in the composition according to the invention is 0.5 to 10% by weight, preferably 1 to 8% by weight, more preferably 1.5 to 6% by weight.

The weight ratio of lemon juice or lemon juice concentrate, to phenoxyethanol is preferably in the range of 1:0.1 to 1:0.8, more preferably in the range of 1:0.3 to 1:0.6.

Surprisingly, it has been shown that excellent cleaning effects of the skin can be achieved by the combinatorial use of a lemon juice, with phenoxyethanol.

The composition according to the invention contains at least one anionic surfactant with a total content of at least 2% by weight, preferably from 2 to 60% by weight, based on the total composition. Anionic surfactants are surfactants which have a negatively charged functional group. Like all surfactants, anionic surfactants are composed of a polar and a non-polar part. An alkyl residue can act as the non-polar part. The polar functional group can be, for example, a carboxylate group ($—COO^-$), a sulphonate group ($—SO_3^-$) or a sulphate group ($—SO_4^{2-}$).

The anionic surfactant or surfactants are preferably selected from the group consisting of secondary alkane sulphonic acids, secondary alkane sulphonates, alkyl ether sulphates, alkyl sulphates and any mixtures thereof.

Alkyl sulphates are water-soluble salts or acids of the formula $ROSO_3M$, where R is a $C_{10}$-$C_{24}$-hydrocarbon radical, preferably a $C_{10}$-$C_{20}$-alkyl or hydroxyalkyl radical, particularly preferably a $C_{12}$-$C_{18}$-alkyl or hydroxyalkyl radical. M is hydrogen or a cation, for example an alkali metal cation such as sodium or potassium, or ammonium or substituted ammonium. Examples of a substituted ammonium are methyl, dimethyl and trimethyl ammonium cations, alkanol ammonium, and quaternary ammonium cations such as tetramethylammonium and dimethyl piperidinium cations and quaternary ammonium cations derived from alkylamines such as ethylamine, dimethylamine, triethylamine and mixtures thereof.

The alkyl ether sulphates (in the prior art these are also referred to as fatty alcohol ether sulphates, INCI alkyl ether sulphates) are water-soluble salts or acids of the formula $RO(A)_m SO_3M$, where R is an unsubstituted $C_8$-$C_{18}$-alkyl or hydroxyalkyl radical, preferably a $C_{10}$-$C_{16}$-alkyl or hydroxyalkyl radical, particularly preferably $C_{12}$-$C_{14}$-alkyl or hydroxyalkyl radical. A is an alkylene oxide moiety, preferably an ethylene oxide, m is a number greater than 0, preferably between about 2 and about 9 (degree of ethoxylation ranging from EO 2 to 9), more preferably between about 3 and about 7 (degree of ethoxylation ranging from EO 3 to 7), and M is a hydrogen atom or a cation, for example sodium, potassium, ammonium or a substituted ammonium cation. Specific examples of substituted ammonium cations include methyl, dimethyl, trimethylammonium and quaternary ammonium cations such as tetramethylammonium and dimethyl piperidinium cations, as well as those derived from alkylamines such as ethylamine, dimethylamine, triethylamine or mixtures thereof. Examples are $C_{10}$-$C_{14}$-fatty alcohol ether sulphates in which the EO content is 2, 3, 4, 5, 6, 7, 8 or 9 moles per mole of the fatty alcohol ether sulphate and in which M is sodium or potassium.

Secondary alkane sulphonates are the salts of secondary alkane sulphonic acids. In these anionic surfactants, the alkyl group can be either saturated or unsaturated, branched or linear and optionally substituted with a hydroxyl group. The sulphonate group may be at any position on the C-chain, with the primary methyl groups at the beginning and end of the chain having no sulphonate groups. The preferred secondary alkane sulphonates contain linear primary and/or secondary alkyl chains each having 10 to 24 carbon atoms, preferably 10 to 20 carbon atoms and particularly preferably 12 to 18 carbon atoms. The cation is, for example, sodium, potassium, ammonium, mono-, di- or triethanolammonium. Mixtures of different cations can also be used.

Exemplary alkyl radicals of the above-mentioned anionic surfactants with 10 to 13 carbon atoms are the n-decyl, the n-undecyl and the n-dodecyl group. Primary or secondary chains of length ($C_8$-$C_{18}$) are illustrated by the following groups: n-octyl, 2-octyl, n-nonyl, 2-nonyl, n-decyl, 2-decyl, n-undecyl, 2-undecyl, n-dodecyl, 2-dodecyl, n-tridecyl, 2-tridecyl, n-tetradecyl-, 2-tetradecyl, n-pentadecyl, 2-pentadecyl, n-hexadecyl, 2-hexadecyl, n-heptadecyl, 2-heptadecyl, n-octadecyl and 2-octadecyl groups.

Among the anionic surfactants, the alkyl ether sulphates have proved to be particularly advantageous. Particularly preferred anionic surfactants according to the invention are therefore alkyl ether sulphates or their sodium salts. Even more preferred are alkyl ether sulphates with 8 to 18 carbon atoms, most preferably with 12 to 14 carbon atoms, or their salts, preferably their sodium salts.

The anionic surfactant or the anionic surfactant mixture comprised in the composition according to the invention, preferably the preferred secondary alkane sulphonic acids, secondary alkane sulphonates, alkyl ether sulphates and/or alkyl sulphates, are comprised in the compositions according to the invention individually or in any combination with one another in a proportion of 2 to 60% by weight by weight, in particular in a proportion of 4 to 50% by weight, very preferably in a proportion of 5 to 40% by weight, based on the total composition.

Preferably, the anionic surfactant or the anionic surfactant mixture comprises at least one of the alkyl ether sulphates described above. In the surfactant mixtures preferably in combination with at least one alkyl sulphate or with at least one secondary alkane sulphonate or secondary alkane sulphonic acid. The alkyl sulphate or alkyl sulphates and/or secondary alkane sulphonate, secondary alkane sulphonic acid or multiple secondary alkane sulphonates and/or secondary alkane sulphonic acids are again preferably as described above.

In the anionic surfactant mixtures, the alkyl ether sulphate (s) is/are preferably present in a proportion of 1 to 30% by weight, preferably in a proportion of 2 to 20% by weight, very preferably in a proportion of 3 to 15% by weight, based on the total composition, and the at least one alkyl sulphate or the at least one secondary alkane sulphonate or the at least one secondary alkane sulphonate is/are present in a proportion of 1 to 30% by weight, preferably in a proportion of 2 to 20% by weight, very preferably in a proportion of 3 to 15% by weight, based on the total composition.

The composition according to the invention further comprises water (as solvent).

The proportion of water is the remainder to 100% by weight (ad. 100% by weight), based on the total composition of the cleaning agent according to the invention. That is to say, the proportions by weight of the essential and optional constituents, if any, of the composition are always chosen so that the total is 100% by weight.

The composition according to the invention is preferably a liquid acidic composition. The composition according to the invention preferably has an acidic pH in the range of 4.75 to 5.75. For example, the pH of the composition may be 5.5.

The composition according to the invention may further comprise at least one hydrotropic agent. The hydrotropic agent is or preferably comprises toluene sulphonate and/or cumene sulphonate and/or sodium or potassium salts thereof. The hydrotropic agent or mixture of hydrotropic agents, for example the toluene sulphonate and/or the cumene sulphonate and/or their sodium or potassium salts or a mixture with toluene sulphonate and/or cumene sulphonate and/or their sodium or potassium salts, is preferably present in the composition according to the invention in a proportion of 0.5 to 3% by weight. Even more preferably, the optional proportion of hydrotropic agent is 1 to 2.8% by weight, even more preferably 1.2 to 2.6% by weight, in each case based on the total composition.

The agent according to the invention may optionally also contain one or more usual additives or auxiliary agents. Suitable substances and substance mixtures are well known to the skilled person and can be obtained commercially. The additives and auxiliary agents may be, for example, conventional formulation aids, buffer substances, scaffolding substances, preserving agents, thickeners, foam stabilisers, foaming aids, humectants, etc., which are acceptable for the intended purpose. Thus, the composition according to the invention may contain one or more thickening agents. Thickening agents suitable for this purpose are generally known to the skilled person and are commercially available. Particularly preferred thickening agents are celluloses and cellulose derivatives. These thickening agents have been found to be advantageous in combination with the other essential and optional components of the composition according to the invention. Hydroxypropyl methylcellulose is particularly preferred because of favourable technical production properties. According to the invention, the thickener(s) may be included in the composition according to the invention either individually or in combination with other additives and auxiliary agents. The thickener(s) is/are preferably present in the composition according to the invention in a proportion of from 0.05 to 1% by weight, more preferably from 0.1 to 0.8% by weight, even more preferably from 0.15 to 0.6% by weight. The use of a thickening agent is advantageous because it allows the applied amount of agent to adhere to the hands during the washing method. With a low viscosity agent, on the other hand, there is the possibility of losing some of the cleaning liquid when it is applied to the skin.

Humectants are substances or mixtures of substances which confer on cosmetic or dermatological preparations the property of reducing the release of moisture from the horny layer after application or spreading on the skin surface and/or of positively influencing the hydration of the horny layer. Glycerine, lactic acid and hyaluronic acid may be mentioned by way of example, but not in a restrictive manner.

Pharmaceutically and/or cosmetically acceptable foam stabilisers and foaming aids are basically known to the skilled person. They can for example or preferably be selected from the group consisting of amine oxides, in particular alkyl amine oxides. The alkyl amine oxides preferably contain alkyl radicals with a chain length of 14 to 24 carbon atoms. According to the invention, a preferred foam booster is cocos propyl amine oxide or cocos fatty acid amidopropyldimethyl amine oxide or cocamido-propyl amine oxide or cocos fatty acid amidopropyldimethyl ammonium oxide with different chain lengths (CAS No. 68155-09-9). The use of a foam booster is advantageous because the foam formed from the agent adheres well to the skin during cleaning and thus leads to thorough cleaning.

According to one embodiment of the invention, the composition according to the invention is free of odorants and/or perfume. Additionally or alternatively, the composition according to the invention is free of alcohol, preferably monohydric Ci-05 alcohols. For the purposes of the present invention, alcohols mean organic compounds having one or more hydroxy groups attached to different aliphatic carbon atoms. Exemplary, but not limiting, monohydric alcohols are methanol, ethanol and propanol.

Further alternatively or in addition to the odorants, perfumes and/or alcohols, the composition according to the invention may be free of such components which may adhere to the hands in a residue-relevant manner and thus could be transferred to plants, plant products and/or food via contact with the hands.

The indication "free from" means, for the purposes of the present disclosure, that the proportion of such constituents in the total composition is 0 to less than 0.01% by weight. Preferably, the maximum allowable limit is 0.008% by weight, even more preferably 0.006% by weight and even further preferably 0.004% by weight, in each case based on the cleaning composition. Most preferably, the proportion of such constituents in the composition is 0% by weight. Any unavoidable impurities are to be disregarded here.

Furthermore, it is preferred according to the invention that the components of the agent are to be selected in such a way that the agent is biologically well degradable and dermatologically well tolerated. Through the combinations of ingredients described above, it has been surprisingly shown that an outstanding cleaning performance can be achieved without aggressive agents and at the same time a pleasant skin feeling, while at the same time preserving the acid mantle of the skin. The composition according to the invention is thus particularly skin-compatible and nourishing, without the need to add additional skin moisturizing agents and/or skin-nourishing components. However, the use of skin moisturizing agents and/or skin-nourishing components is not excluded in principle according to the invention.

According to a preferred embodiment, the composition according to the invention comprises the following components:

| |
|---|
| 10-20% by weight of a lemon juice or a lemon juice concentrate, |
| 1-5% by weight phenoxyethanol, |
| 5-25% by weight of an alkyl sulphate containing 12 to 18 carbon atoms, preferably a sodium alkyl sulphate, |
| 5-25% by weight of an alkyl ether sulphate having 10 to 14 carbon atoms, preferably with a degree of ethoxylation in the range of EO 3 to 9, |
| 0-5% by weight, preferably |
| 1-4% by weight of at least one hydrotropic agent, preferably toluene sulphonate and/or cumene sulphonate and/or their sodium or potassium salts, and ad 100% by weight water. |

In addition to the ingredients mentioned for this preferred embodiment of the agent according to the invention, such a cleaning agent may optionally contain one or more customary additives and auxiliary agents.

Also comprised within the scope of the present invention are those compositions or agents which, with the exception of usual impurities, consist only of the above-mentioned essential components, and optionally one or more of the optional components.

According to another preferred embodiment, the composition according to the invention comprises the following components:

| |
|---|
| 5-15% by weight of a lemon juice or lemon juice concentrate, |
| 1-5% by weight phenoxyethanol, |
| 1-6% by weight of a secondary alkyl sulphonate having 12 to 18 carbon atoms, preferably a sodium alkyl sulphonate, |
| 1-6% by weight of an alkyl ether sulphate having 10 to 14 carbon atoms, preferably with a degree of ethoxylation in the range of EO 3 to 9, |
| 0-5% by weight preferably |
| 1-4% by weight of at least one hydrotropic agent, preferably toluene sulphonate and/or cumene sulphonate and/or their sodium or potassium salts, and |
| ad 100% by weight water. |

In addition to the ingredients mentioned for this preferred embodiment of the agent according to the invention, such a composition may optionally contain one or more usual additives and auxiliary agents.

Also included within the scope of the present invention are those compositions or agents which, with the exception of usual impurities, consist only of the above-mentioned essential components, and optionally one or more of the optional components.

The agent according to the invention is a liquid one-component product which can be formulated as a ready-to-use product, but which, on the other hand, can also be formulated as a product concentrate from which a diluted use solution can be prepared, which can then preferably contain 1 to 30% by weight, even more preferably 2 to 20% by weight of the agent. The dilution of the agent to the working solution is preferably carried out with water. The present application therefore also relates to the finished working solution thus obtained.

The ready-to-use active ingredient solution, regardless of whether it is produced from a concentrate or is already originally formulated as such, is preferably formulated either as a rub-in product or as a hand/skin wash. A rub-in product is first rubbed into or onto the skin/hands to clean them and, after an exposure time of preferably 30 seconds to 2 minutes, is removed with a paper towel and/or textile cloth, whereby the cloth can also be a wet cloth or a cloth soaked in water, for example. In contrast, a hand/skin wash is for a washing-up procedure, for example at the sink. To clean the skin/hands, a hand/skin wash is first rubbed into or onto the skin/hands and then washed off under running water after an exposure time of preferably 30 seconds to 2 minutes.

However, the composition according to the invention can also be used with the aid of a wet cosmetic and/or dermatological cloth. The present invention therefore also comprises cloths which are moistened or impregnated with the composition according to the invention.

The ready-to-use wet or impregnated cloths thus comprise two components, namely a cloth composed of materials such as paper and/or a wide variety of mixtures of natural or synthetic fibres, and an impregnating solution. The impregnating solution is the composition according to the invention, whether in undiluted or diluted form.

Among other things, the cloths allow efficient and gentle cleaning of the skin, especially the hands, especially in the absence of (running) water.

In general, all organic and inorganic fibrous materials on a natural and synthetic basis can be used as starting materials for the dry cloth. Examples include cellulose-based pulp materials, woven fabrics, for example cotton fabrics, and nonwoven materials. The nonwoven material may be, for example, a hydroentangled and/or hydro-embossed nonwoven. Exemplary starting materials for woven and nonwoven fabrics include viscose, cotton, jute, hemp, sisal, silk, wool, polypropylene, polyester, polyethylene terephthalate (PET), aramid, nylon, polyvinyl derivatives, polyurethanes, polylactide, polyhydroxyalkanoate, cellulose esters and/or polyethylene, as well as mineral fibres such as glass fibres or carbon fibres. However, the present invention is not limited to the aforementioned materials, but a variety of other materials and fibres may be used to produce the dry cloth, provided that the cloths thus obtained are suitable for cosmetic and/or dermatological use.

The thickness of the dry, i.e. not yet moistened or soaked, cloth is preferably 0.2 mm to 1.5 mm, in particular 0.4 mm to 0.9 mm. However, other thicknesses are also provided according to the invention, provided that the cloth ensures the necessary mechanical stability and/or flexibility for cleaning.

The materials or fibres used to form the cloth preferably have a water absorption rate of more than 60 mm/[10 min] (measured with EDANA Test 10.1-72), in particular more than 80 mm/[10 min]. Additionally or alternatively, the materials or fibres used to form the cloth preferably have a water absorption capacity of more than 5 g/g (measured with EDANA Test 10.1-72), in particular more than 8 g/g.

The cloths can be surface-textured. This embossing can be achieved, for example, by mechanical embossing using calender rollers or by water jet embossing.

By structuring, a uniform sequence of elevations and depressions can be formed in the material. In combination with the impregnating solutions according to the invention, this structuring enables both better access to depressions in the human skin due to its elevations and an increased dirt-holding capacity due to its structural valleys. Overall, this leads to a significantly improved cleaning performance.

In relation to the non-surface-structured cloth, the thickness of the cloth with the elevations created by the surface structuring can advantageously be approximately twice as large. In preferred embodiments, the surface-textured cloth is between 5% and 50%, very preferably between 10% and 25%, thicker than the non-surface-textured cloth.

The present invention further relates to the use of a composition containing lemon juice for removing organic and/or inorganic soils from the skin, in particular from the hands. The composition used according to the invention comprises at least 5% by weight, preferably 5-30% by weight, of lemon juice or of a lemon juice concentrate 0.5-10% by weight phenoxyethanol, at least 2% by weight, preferably 2-60% by weight, of an anionic surfactant or a mixture of two or more anionic surfactants, and ad 100% by weight water.

The use of such an agent allows for a gentle but effective removal of such contaminants and/or decontamination of the skin, especially the hands.

With regard to the chemical nature and/or proportions of the individual ingredients and preferred embodiments thereof, reference is made to the corresponding disclosure in connection with the composition as such and reference is made thereto.

According to a preferred form of use according to the invention, the contaminants to be removed are contaminants containing chlorophyll and/or other plant dyes and/or plant juices/extracts, as well as plant parts, such as flower pollen and/or plant dusts.

Chlorophylls are natural pigments formed by organisms that carry out photosynthesis. They are thus present in all green parts of plants. The term "coloured components" as used in the context of the present invention means or includes other photosynthetic pigments and coloured secondary plant ingredients.

Plant juices or plant extracts are produced, for example, during the harvesting, packaging or processing of plant products, especially tomatoes, peppers and/or cucumbers. These impurities are difficult to remove from the skin due to their chemical composition. Surprisingly, it has been shown that an agent containing lemon juice as described above is particularly suitable for effectively and gently removing such impurities from the skin. In addition, the use of the agent can take into account aspects relating to food law and/or the protection of employees.

Thus, in one embodiment of the invention, the use according to the invention relates to the use of one of the compositions according to the invention described above for removing contaminants containing chlorophyll and/or other plant dyes and/or for removing plant juices/extracts from the skin. Surprisingly, the compositions according to the invention described herein provide at least as effective cleaning, but they are significantly less stressful for the skin and thus easier to handle.

According to the invention, the organic and/or inorganic contaminants to be removed from the skin may also be, or in addition to, the contaminants containing chlorophyll and/or other plant pigments and/or the plant juices/extracts and/or the plant parts, such as pollen and/or plant dusts, undesirable contaminants on the skin. The contaminants are bacterial phytopathogens, fungal phytopathogens, viral phytopathogens, fertiliser residues, herbicides, bactericides, fungicides, virucides, germination inhibitors or any mixtures thereof. Fertilisers, plant protection products and germination inhibitors, for example, are used on a large scale in crop production. The residues left on the plant parts or washed off residues can thus lead to contamination of the skin of employees.

Also for this type of contaminants, the composition according to the invention has proven to be particularly effective in removing them effectively and gently from the skin of contaminated persons.

The use according to the invention relates to the cleaning of the skin, in particular the skin of the hands and arms of the persons concerned.

In the application according to the invention, the agent is applied either directly as a liquid or after prior dilution of the agent. The dilution of the composition is carried out with water t. The application concentration of the diluted composition is preferably 1 to 30%, preferably 2 to 20%, based on the composition. The pH of the diluted, ready-to-use composition is preferably in the range of 4.75 to 5.75.

As already mentioned above, the ready-to-use agent can be used as a rub-in product or as a hand/skin wash. For both application variants, the exposure time of the agent according to the invention to the skin surface to be cleaned is preferably at least 10 seconds, preferably at least seconds, even more preferably at least 30 seconds and very particularly preferably at least seconds. Furthermore, it is preferred that the maximum exposure time of the agent according to the invention on the skin surface is 5 minutes, preferably 4 minutes, 3 minutes or 2 minutes. The high compatibility of the agent according to the invention already mentioned above has proved to be particularly advantageous in this respect and makes the exposure times possible. After the exposure time, the agent is washed off the skin surface (wash-off procedure) or removed in another way, for example with a paper towel and/or textile cloth (rub-in procedure), whereby the cloth can also be wet or soaked with water. Of course, several successive cleanings of the same skin surface are also possible, as required, and are comprised in the scope of the present invention.

However, the agent according to the invention can also be used with the aid of the wet or soaked cloths described above.

The present invention further also provides a method for removing organic and/or inorganic contaminants from the skin, preferably from the hands, the method comprising the steps of:

providing a lemon juice-containing composition comprising 5-30% by weight of lemon juice or a lemon juice concentrate, 0.5-10% by weight of phenoxyethanol, 2-60% by weight of an anionic surfactant or a mixture of two or more anionic surfactants and ad 100% by weight of water.

applying the provided lemon juice-containing composition to a skin surface soiled with organic and/or inorganic contaminants, and cleaning the skin surface.

In the method according to the invention, the application of the composition takes place either directly as a liquid or after prior dilution, for example with water. Foam formation can be subsequently triggered by a mechanical action.

The cleaning of the skin surface, e.g. of the hands and arms, can be done by a washing procedure, as it is done in normal body hygiene, e.g. when washing hands with a commercial soap. Alternatively, a rub-in procedure is also conceivable. In this case, the agent is spread and rubbed onto the skin surface to be cleaned, for example the hands and arms, without water, and then removed with a paper towel and/or textile cloth, whereby the cloth can also be wet or soaked with water. Alternatively, the application of the composition can be carried out by means of the wet or soaked cloth described above.

With regard to the exposure time of the agent on the skin surface to be cleaned, reference is made to the corresponding explanations in the context of the use according to the invention—for the two application forms rub-in procedure or wash-off procedure. The times apply equally to the use according to the invention and the method according to the invention.

After the exposure time, the agent is washed off or otherwise removed from the skin surface. The step of washing off or removing the agent can be omitted when using the wet or soaked cloths. Of course, several successive cleanings are possible as required and are comprised within the scope of the present invention. The method according to the invention may thus comprise the further steps of allowing the applied composition to react, preferably with the above-mentioned exposure times, and/or the step of washing off or otherwise removing the applied composition, optionally after it has reacted.

According to the invention, it is also provided that the composition is diluted to a desired application concentration in an upstream method step prior to its application as a solution. The dilution of the composition is carried out with water. The application concentration of the diluted composition is then preferably 1 to 30% by weight, preferably 2 to 20% by weight of the original composition. The dilution of the composition to the use solution is carried out with water. The method according to the invention may thus comprise the further step, preceding the application, of diluting the composition to be applied, preferably to the above-mentioned application concentrations.

In a preferred embodiment, the method according to the invention thus comprises the steps of Providing a lemon juice-containing composition composed as described above, If necessary, diluting the provided lemon juice containing composition to an application concentration of preferably 1 to 30% by weight, preferably 2 to 20% by weight, with water, Application of the composition, diluted if necessary, to a skin surface to be cleaned, preferably the hands and/or arms, allowing the applied composition to react, preferably for a period of 10 seconds to 5 minutes, and If necessary, wash off or remove the applied composition.

With regard to preferred embodiments of the composition used in the method according to the invention, reference is made to the above explanations on the composition as such and reference is made thereto.

According to one embodiment of the method of the invention, the lemon juice-containing composition is used for removing contaminants containing chlorophyll and/or other plant dyes and/or for removing plant juices/extracts.

In another preferred embodiment, a method for removing contaminants on the skin is provided, wherein the contaminants are preferably selected from the group consisting of bacterial phytopathogens, fungal phytopathogens, viral phytopathogens, fertilizer residues, herbicides, bactericides, fungicides, antivirals, and any mixtures thereof.

Adherence of plant juices/extracts to the skin may not only be undesirable for purely cosmetic reasons, but the plant juices/extracts may under certain circumstances also cause skin irritation and/or allergic reactions in the persons concerned. Residues or adhesions of fertilisers, herbicides, bactericides, fungicides, virucides, germination inhibitors and/or pathogens on, for example, the hands of employees can be problematic in meristem or plant breeding farms and plant-producing farms, among others, not only because they can thus be distributed uncontrollably to other crops in the farm, but also from a health aspect for the protection of employees. Incorporation of these substances must be avoided.

It is further an object of the present invention to provide a lemon juice-containing composition, composed as described above, for use in a method of hygienically cleaning and decontaminating the skin and/or hands of a user.

The skin, for example the hands, is/are freed from organic and/or inorganic soiling with the aid of the composition, and thus, for the above-mentioned reasons, a preventive measure is carried out to protect the health of people who are exposed to such soiling.

One embodiment relates to the composition for use in a method for cleaning the skin and/or hands of contaminants containing chlorophyll and/or other plant dyes and/or for removing plant juices/extracts.

Another embodiment relates to the composition for use in a method of cleaning and decontaminating the skin and/or hands from contaminants, wherein the contaminants are preferably selected from the group consisting of bacterial phytopathogens, fungal phytopathogens, viral phytopathogens, fertilizer residues, herbicides, bactericides, fungicides, antivirals, germicides and any mixtures thereof.

Likewise, the present invention relates to a lemon juice-containing composition composed as described above for use in a method of cleaning the skin and/or hands to prevent skin irritation and/or allergic reactions that may be caused by plant juices/extracts. Further according to the invention, a lemon juice-containing composition composed as described above is for use in a method for preventing incorporation of contaminants, said contaminants preferably being selected from the group consisting of bacterial phytopathogens, fungal phytopathogens, viral phytopathogens, fertilizer residues, herbicides, bactericides, fungicides, antivirals, germicides and any mixtures thereof.

With regard to preferred embodiments of the composition used, the method and manner of application of the composition, reference is made to the above explanations on the composition as such and on the use according to the invention and reference is made thereto.

The following examples illustrate the invention without, however, limiting it thereto; all designations are in % by weight unless otherwise indicated.

EXAMPLES

The following examples and explanations of the composition are intended to clarify, but not limit, the objects according to the invention.

The synergistic effect between lemon juice, phenoxyethanol and the anionic surfactants can be illustrated particularly clearly using the example of orange juice, grapefruit juice (not according to the invention) and lemon juice.

Freshly squeezed juice of ripe lemons, oranges and grapefruits (*Citrus grandis*) was freed from the pulp by filtration. The total acid content of the juices, whose acidic components are predominantly composed of citric acid and only to a very small extent of iso-citric acid, ascorbic acid and other acidic components, was determined by titration from the filtrate.

The titration results were converted to citric acid, resulting in a mean theoretical concentration of 4.8% by weight in the filtered juice, based on 3 to 8% by weight citric acid. The pH value of the lemon juice was determined to be pH 2.34, that of the grapefruit juice to be 2.68 and that of the orange juice to be pH 3.05.

The analytical classification of the juices served as a standardisation for the repeatability of the investigations.

The serum of the juices consisted of clear, light to intense yellow, low-odour liquids, which were mixed with phenoxyethanol and surfactants to produce the agents of the invention and used as ready-to-use solutions for cleaning the hands.

Example 1: Agent Containing Lemon Juice

| Components | Parts by weight (wt./wt.) |
|---|---|
| Alkyl($C_{12}$-$C_{18}$)sulphonate-Na | 18.00 |
| Na-($C_{13}$)-alkyl ether sulphonate | 20.00 |
| Cumene sulphonate-K | 2.00 |
| Phenoxyethanol | 4.00 |
| Lemon juice | 15.00 |
| Water | 41.00 |

Example 2: Agent Containing Lemon Juice

| Components | Parts by weight (wt./wt.) |
|---|---|
| Sec.-alkyl($C_{12}$-$C_{18}$)-sulphonate -Na | 10.00 |
| Na-dodecyl ether sulphate | 10.00 |
| Toluene sulphonate-K | 3.00 |
| Phenoxyethanol | 2.00 |
| Lemon juice | 15.00 |
| Water | 60.00 |

Example 3: Agent Containing Lemon Juice

| Components | Parts by weight (wt./wt.) |
|---|---|
| Sec.-alkyl($C_{12}$-$C_{18}$)-sulphonate-Na | 3.00 |
| Na-dodecyl ether sulphate | 3.00 |
| Toluene sulphonate-K | 2.00 |
| Phenoxyethanol | 2.00 |
| Lemon juice | 10.00 |
| Water permuted | 80.00 |

In the preparation of example formulations 1 to 3, the water, preferably purified water, is first added and the citrus fruit juice is then dissolved in it. The surfactants and the other components are then added to this solution, and if necessary further water to 100% by weight is added and stirred. The result is a clear liquid.

It has been shown that the exemplary compositions according to the invention could effectively and gently remove chlorophyll-containing soiling from the skin by washing the hands with a contact time of 30 seconds. The epicutaneous test for testing the skin irritating effect showed a good skin tolerance of the test solutions according to the invention.

Comparable positive results were achieved in the removal of fertiliser residues. Here, too, the cleaning was very effective and gentle.

What is claimed is:

1. A composition for cleaning skin and/or hands comprising:

A) from 5-30% by weight of lemon juice or lemon juice concentrate;

B) from 0.5-10% by weight of phenoxyethanol;

C) from 2-60% by weight of an anionic surfactant selected from the group consisting of secondary alkane sulphonic acids, secondary alkane sulphonates, alkyl ether sulphates, alkyl sulphates, and their sodium or potassium salts and any mixtures thereof;

D) from 0.5 to 3% by weight of toluene sulphonate and/or cumene sulphonate and their sodium or potassium salts;

E) optionally from 0.1-5% by weight of a non-ionic surfactant or of a mixture of two or more non-ionic surfactants;

F) optionally from 0.05 to 1% by weight of one or more thickening agents; and

G) water to 100% by weight.

2. The composition according to claim 1, wherein the weight ratio of lemon juice or lemon juice concentrate to phenoxyethanol is from 1:0.1 to 1:0.8.

3. The composition according to claim 1 further comprising the non-ionic surfactant or the mixture of two or more non-ionic surfactants, wherein the non-ionic surfactant is a fatty alcohol ethoxylate, or the mixture comprises at least one fatty alcohol ethoxylate.

4. The composition according to claim 1, further comprising the one or more thickening agents.

5. The composition according to claim 1, wherein the composition is formulated as a ready-to-use active ingredient solution.

6. A wet cloth comprising a cloth of a cellulose-based pulp material, a woven fabric and/or a non-woven fabric, wherein the cloth is wetted with the composition of claim 1 as an impregnating solution.

7. A wet cloth according to claim 6, wherein the weight ratio of the unimpregnated cloth to the impregnating solution is selected from the range of 1:1 to 1:5.

8. A method for removing organic and/or inorganic soiling from the skin, the method comprising applying the composition according to claim 1 to the skin.

9. The method according to claim 8, wherein the soiling to be removed is a contaminant containing chlorophyll and/or other plant dyes and/or plant juices/extracts and/or other plant parts.

10. The method according to claim 8, wherein the soiling to be removed is contaminants on the skin, said contaminants being selected from the group consisting of bacterial phytopathogens, fungal phytopathogens, viral phytopathogens, fertilizer residues, herbicides, bactericides, fungicides, virucides, germicides and any mixtures thereof.

11. The method according to claim 8, wherein the composition is applied as a diluted aqueous solution, the composition being adjusted by dilution with water to active ingredient concentrations in the range from 0.5 to 50%.

12. The method according to claim 8, wherein the composition is applied as a ready-to-use rub-in product or as a hand/skin wash.

13. A method for removing organic and/or inorganic soiling from the skin, the method comprising rubbing the skin with the wet cloth according to claim 6 wherein the soiling is contaminants on the skin selected from the group consisting of bacterial phytopathogens, fungal phytopathogens, viral phytopathogens, fertilizer residues, herbicides, bactericides, fungicides, virucides, germicides and any mixtures thereof, and/or wherein the contaminants to be removed are contaminants containing chlorophyll and/or other plant dyes and/or plant juices/extracts and/or other plant parts.

14. The composition according to claim 2, wherein the weight ratio of lemon juice or lemon juice concentrate to phenoxyethanol is from 1:0.2 to 1:0.6.

15. The composition according to claim 5, wherein the ready-to-use solution is either a rub-in product or a hand/skin wash.

* * * * *